(12) United States Patent
Benk et al.

(10) Patent No.: US 11,992,670 B2
(45) Date of Patent: May 28, 2024

(54) BLOOD PUMP

(71) Applicant: ResuSciTec GmbH, Freiburg (DE)

(72) Inventors: Christoph Benk, Freiburg (DE); Lion Heimgartner, Freiburg (DE)

(73) Assignee: RESUSCITEC GMBH, Freiburg (DE)

( * ) Notice: Subject to any disclaimer, the term of this patent is extended or adjusted under 35 U.S.C. 154(b) by 0 days.

(21) Appl. No.: 18/001,595

(22) PCT Filed: Apr. 21, 2021

(86) PCT No.: PCT/EP2021/060363
§ 371 (c)(1),
(2) Date: Dec. 13, 2022

(87) PCT Pub. No.: WO2022/008114
PCT Pub. Date: Jan. 13, 2022

(65) Prior Publication Data
US 2023/0218885 A1 Jul. 13, 2023

(30) Foreign Application Priority Data
Jul. 7, 2020 (DE) ...................... 10 2020 117 818.2

(51) Int. Cl.
*A61M 60/232* (2021.01)
*A61M 60/419* (2021.01)
(Continued)

(52) U.S. Cl.
CPC ........ *A61M 60/232* (2021.01); *A61M 60/419* (2021.01); *A61M 60/806* (2021.01); *A61M 60/825* (2021.01)

(58) Field of Classification Search
CPC .............. A61M 60/232; A61M 60/419; A61M 60/806; A61M 60/825; A61M 60/422;
(Continued)

(56) References Cited

U.S. PATENT DOCUMENTS 4,589,822 A * 5/1986 Clausen .............. A61M 60/806
415/174.3
4,984,972 A * 1/1991 Clausen .............. A61M 60/825
417/420
(Continued)

FOREIGN PATENT DOCUMENTS

DE 19626224 A1 1/1998
DE 102006036948 A1 2/2008
(Continued)

OTHER PUBLICATIONS

Rau et al. DE 196 26 224 English Machine Trans Espacenet Jan. 2, 1998 (Year: 1998).*

(Continued)

*Primary Examiner* — David E Sosnowski
*Assistant Examiner* — Wayne A Lambert
(74) *Attorney, Agent, or Firm* — Fitch, Even, Tabin & Flannery LLP

(57) ABSTRACT

The invention includes three flushing channels each having a flushing channel longitudinal axis oriented parallel to the rotary shaft, which are distributed evenly around a rotary shaft with each flushing channels including a flushing channel cross-section oriented orthogonally to the rotary shaft. The cross-sections are each kidney-shaped and surround the rotary shaft in sectors.

19 Claims, 6 Drawing Sheets

(51) Int. Cl.
*A61M 60/806* (2021.01)
*A61M 60/825* (2021.01)

(58) Field of Classification Search
CPC .............. A61M 60/178; F04D 29/2266; F04D 29/2272; F04D 29/688
See application file for complete search history.

(56) References Cited

U.S. PATENT DOCUMENTS

| | | | | |
|---|---|---|---|---|
| 5,360,317 A | * | 11/1994 | Clausen | F04D 29/0413 |
| | | | | 415/206 |
| 5,399,074 A | * | 3/1995 | Nose | A61M 60/825 |
| | | | | 417/423.12 |
| 5,405,251 A | * | 4/1995 | Sipin | F04D 29/043 |
| | | | | 417/423.1 |
| 5,443,503 A | * | 8/1995 | Yamane | A61M 60/232 |
| | | | | 600/16 |
| 6,171,078 B1 | * | 1/2001 | Schob | A61M 60/824 |
| | | | | 417/423.1 |
| 6,722,863 B2 | * | 4/2004 | Maeda | A61M 60/422 |
| | | | | 415/206 |
| 7,416,525 B2 | * | 8/2008 | Wampler | F04D 29/628 |
| | | | | 600/16 |
| 8,398,382 B2 | * | 3/2013 | Omori | F04D 29/0467 |
| | | | | 417/423.12 |
| 8,512,012 B2 | * | 8/2013 | Akdis | A61M 60/824 |
| | | | | 417/423.12 |
| 8,814,541 B2 | * | 8/2014 | Omori | F04D 29/0467 |
| | | | | 417/423.1 |
| 9,115,725 B2 | * | 8/2015 | Haefliger | F04D 13/0633 |
| 9,162,018 B2 | * | 10/2015 | Foster | A61M 60/178 |
| 9,616,157 B2 | | 4/2017 | Akdis | |
| 10,428,828 B2 | | 10/2019 | Canatella et al. | |
| 11,786,719 B2 | * | 10/2023 | Busch | F04D 29/4273 |
| | | | | 600/16 |
| 11,801,377 B2 | * | 10/2023 | Li | A61M 60/825 |
| 2004/0091354 A1 | * | 5/2004 | Araki | F04D 29/183 |
| | | | | 415/206 |
| 2007/0249888 A1 | * | 10/2007 | Wu | A61M 1/1678 |
| | | | | 600/16 |
| 2017/0122337 A1 | * | 5/2017 | Itamochi | F04D 29/4273 |
| 2017/0361001 A1 | | 12/2017 | Canatella et al. | |
| 2018/0050140 A1 | | 2/2018 | Siess et al. | |
| 2021/0299432 A1 | * | 9/2021 | Hur | A61M 60/825 |
| 2023/0310831 A1 | * | 10/2023 | Chen | A61M 60/806 |
| | | | | 604/6.11 |

FOREIGN PATENT DOCUMENTS

| | | |
|---|---|---|
| EP | 1727987 A1 | 12/2006 |
| EP | 2051751 A2 | 4/2009 |
| EP | 2566533 A2 | 3/2013 |

OTHER PUBLICATIONS

International Search Report for PCT/EP2021/060363, mailed Jul. 12, 2021; 11 pages.

\* cited by examiner c)

d)

BLOOD PUMP

CROSS-REFERENCE TO RELATED APPLICATIONS

Reference is made to PCT/EP2021/060363 filed Apr. 21, 2021, and German Patent Application No. 10 2020 117 818.2 filed Jul. 7, 2020, which are incorporated herein by reference in their entirety.

BACKGROUND OF THE INVENTION

Field of the Invention

The invention relates to a blood pump with a pump housing comprising a bottleneck-shaped flow inlet region in which there is a blade assembly mounted for conjoint rotation on a rotatably mounted rotary shaft. The blade assembly encloses a main flow channel together with the pump housing, and has n blades, which are oriented radially to the rotary shaft, with each blade having a flat shape and arranged around the rotary shaft to be equidistant from each other. Downstream of the bottleneck-shaped flow inlet region is a hollow-cylindrical pump housing portion containing a rotary motor within an inner housing. The rotary motor is operatively connected to the blade assembly to rotate via a magnetic coupling. The inner housing together with the pump housing encloses a flow channel. The flow channel continues the main flow channel, and together with the blade assembly encloses a secondary channel, which fluidically communicates with the main flow channel. The secondary channel is fluidically connected to at least one flushing channel which passes through the blade assembly and opens into the bottleneck-shaped flow inlet region. The inner housing additionally has a lower bearing facing the blade assembly for receiving a lower end of the rotary shaft to rotate. The upper end of the rotary shaft is mounted in a bearing sleeve which is within the bottleneck-shaped flow inlet region.

Description of the Prior Art

A blood pump is described in DE 196 26 224 A1. In the pump housing there is a blade assembly which, together with a rotary shaft, is rotatably mounted about an axis of rotation passing centrally through the pump housing. The rotary shaft is rotatably mounted at its rotary shaft ends on upper and lower bearings. The lower bearing is seated on the upper side of an inner housing, which is downstream of the blade assembly within the pump housing, and encloses an electromotive rotary drive, operatively connected via a magnetic coupling to the blade assembly, which conjointly rotates on the rotary shaft.

The helically shaped blade wheels of the blade assembly enclose, together with the inner wall of the pump housing, an axial main flow channel through which blood flows through the blood pump by being pressure-driven. In addition, the blade assembly has a secondary or flushing channel hydraulically connecting the suction side of the blade assembly to the rear side. In this way, blood can enter and flush a rear-side gap between the blade assembly and the inner housing. Dead water regions at the rear side of the blade assembly are effectively avoided.

US published patent application 2018/0050140 A1 discloses a blood pump having an impeller with spiral blades which is penetrated by six "wash out channels", which have at least one tangential directional component and have a substantially circular channel cross-section.

EP 1727 987 B1 describes a blood pump having a blade assembly rotatably mounted within the pump housing via a magnetic bearing. The blades of the assembly can be flat, helical or otherwise curved. The magnetic bearing of the blade assembly makes possible a low-cost and low-wear pump, which in particular provides a bearing of the blade assembly free from contact with the pump housing. Due to the absence of bearing struts connected to the pump housing, blood clot formation in the inflow region of the blood pump can at least be reduced. The blade assembly is only supported by a ball bearing, which is attached to an inner housing surrounding the rotary motor.

A comparable blood pump with magnetic bearing within the blade assembly is described in EP 2 566 533 B1 and has a metal, conical pin connected to the inner housing inside the pump housing for the dissipation of operation-induced frictional heat and on which the blade assembly is rotatably mounted via a ball contour.

All known blood pumps, based on the principle of a rotating blade assembly, use the centrifugal effect of the rotating blade assembly to build up flow and pressure within the blood pump. This effect, in addition to a main flow along the main flow channel radially bounded by the blade assembly as well as the inner housing and the pump housing, causes a series of secondary flows that branch off from the main flow and from there flow is further through intermediate spaces within the pump. In order to prevent the design-related intermediate gap between the blade assembly and the inner housing surrounding the rotary motor from providing a flow dead space and an associated risk of thrombus formation, the blade assembly has a "flushing channel" through which, due to the prevailing pressure conditions, a secondary blood flow passes through the intermediate gap and the flushing channel fluidically connected thereto. Without special precautions, a secondary flow retrograde to the main flow direction is formed through the flushing channel passing through the blade assembly.

SUMMARY OF THE INVENTION

The invention is a blood pump having a pump housing comprising a bottleneck-shaped flow inlet region in which there is a blade assembly mounted for conjoint rotation on a rotatably mounted rotary shaft, which encloses a main flow channel together with the pump housing, and has n of blades, which are oriented radially relative to the rotary shaft. Each blade has a flat shape, and is disposed about the rotary shaft equidistantly to one another, and a hollow-cylindrical pump housing portion, adjoins the bottleneck-shaped flow inlet region downstream thereof, in which a rotary motor is located within an inner housing. The rotary motor is operatively connected to the blade assembly which cause rotation via a magnetic coupling. The inner housing together with the pump housing encloses a flow channel, which continues the main flow channel, and together with the blade assembly encloses a secondary channel, which fluidically communicates with the main flow channel. The secondary channel is fluidically connected to at least one flushing channel which passes through the blade assembly and opens into the bottleneck-shaped flow inlet region. The inner housing additionally has a lower bearing facing the blade assembly for receiving a lower end of the rotary shaft in a rotatable manner. The upper end of the rotary shaft is mounted in a bearing sleeve which is located in the bottleneck-shaped flow inlet region so that the efficiency of the blood pump is improved.

The blood volume conveyed by the blood pump is achieved with a lower energy input. In particular, the objective is to significantly reduce the operating speed of the rotatably driven blade assembly without reducing the blood volume conveyed in comparison to known blood pumps. With the goal to achieve a more economical operation of the blood pump and an associated, desirable reduction of the operating speed, the blood transport realized with the blood pump is furthermore achieved more gently.

The blood pump according to the invention has three separate flushing channels. Each channel which has a flushing channel longitudinal axis oriented parallel to the rotary shaft, which are distributed evenly around the rotary shaft. Each of the three flushing channels has a flushing channel cross-section oriented orthogonally to the rotary shaft with the cross-sections each being kidney-shaped and surrounding the rotary shaft in different sectors.

Based on a large number of flow tests with differently designed blood pumps, it was possible to find the above blood pump design with optimized flow-dynamic properties, which are reflected in particular that the largest delivery volume can be achieved at a given rotational speed due to the special choice of shape and number of flushing channels oriented parallel to the flushing channel longitudinal axis in conjunction with a number m of blades each formed to be flat, which extend radially from the rotary shaft and are equidistant from each other around the rotary shaft. In comparison to known blood pumps of the same size, the blood pump according to the invention is able to handle a given delivery volume at a lower rotational speed, whereby the blood flowing through the blood pump is subjected to less mechanical stress.

Preferably, the kidney-shaped flushing channel cross-sections are each enclosed by a peripheral edge which has a radially outer convex peripheral contour facing away from the rotary shaft and a radially inner concave peripheral contour facing towards the rotary shaft. In this case, the concave peripheral contours of the three flushing channel cross-sections each lie on a first virtual circular line arranged centrically to the rotary shaft. The convex peripheral contours of the three flushing channel cross-sections, on the other hand, lie on a second virtual circular line which is centrical to the rotary shaft with the radius of each pump being greater than the radius of the first circular line.

It has proven to be particularly advantageous to arrange six blades evenly distributed around the rotary shaft.

In a particularly preferred embodiment, the six blades each have a radial extent which, in axial projection onto the blade assembly, extends along the rotary shaft from the aforementioned second virtual circular line, which in each case delimits the concave peripheral contours of the flushing channel cross-sections, to a third virtual circular line centrical to the rotary shaft, with the radius of the second virtual circular line being smaller than the radius of the third virtual circular line. Preferably, the radius of the third circular line corresponds at most to the radius of the circular circumferential edge of the blade assembly in axial projection onto the rotary shaft.

In an alternative embodiment of the blood pump, the six blades are each divided into a first and a second group, with regard to their shape and size as well as their arrangement on the blade assembly. Thus, three of the six blades of the first group, which are referred to as primary blades, each have a radial extent which, in axial projection onto the blade assembly extending along the rotary shaft from the first virtual circular line, which delimits the aforementioned concave peripheral contours of the kidney-shaped flushing cross-sections, to a third virtual circular line which is arranged centrically to the rotary shaft and which, as in the aforementioned case, corresponds at most to the radius of the circular circumferential edge of the blade assembly.

The three blades belonging to the second group, referred to as secondary blades, on the other hand, each have a radial extent which, in an axial projection onto the blade assembly, extends along the rotary shaft from the second virtual circular line to the third virtual circular line arranged centrically to the rotary shaft. In this case, the primary and secondary blades are each arranged in alternating order around the rotary shaft. Further constructional features and design details in this regard can be found in the further description with reference to the figures of the drawings.

Preferably, moreover, the upper and lower bearings, in which the upper and lower ends of the rotary shaft, respectively, are joined rotatably but in an axially fixed manner, are made of a ceramic or abrasion-resistant plastics material, preferably an ultrahigh molecular (UHM) plastic. The lower bearing attached to the inner housing preferably includes a pot-shaped inlay element which is fixedly joined to the inner housing and into which the lower end of the rotary shaft opens in a rotatable and axially fixed manner and is made of a different material than that from which the inner housing is made.

BRIEF DESCRIPTION OF THE DRAWINGS

Without limiting the general concept of the invention, the invention is described below by way of example on the basis of preferred exemplary embodiments with reference to the drawings, in which.

DETAILED DESCRIPTION OF THE INVENTION

Figure 1:
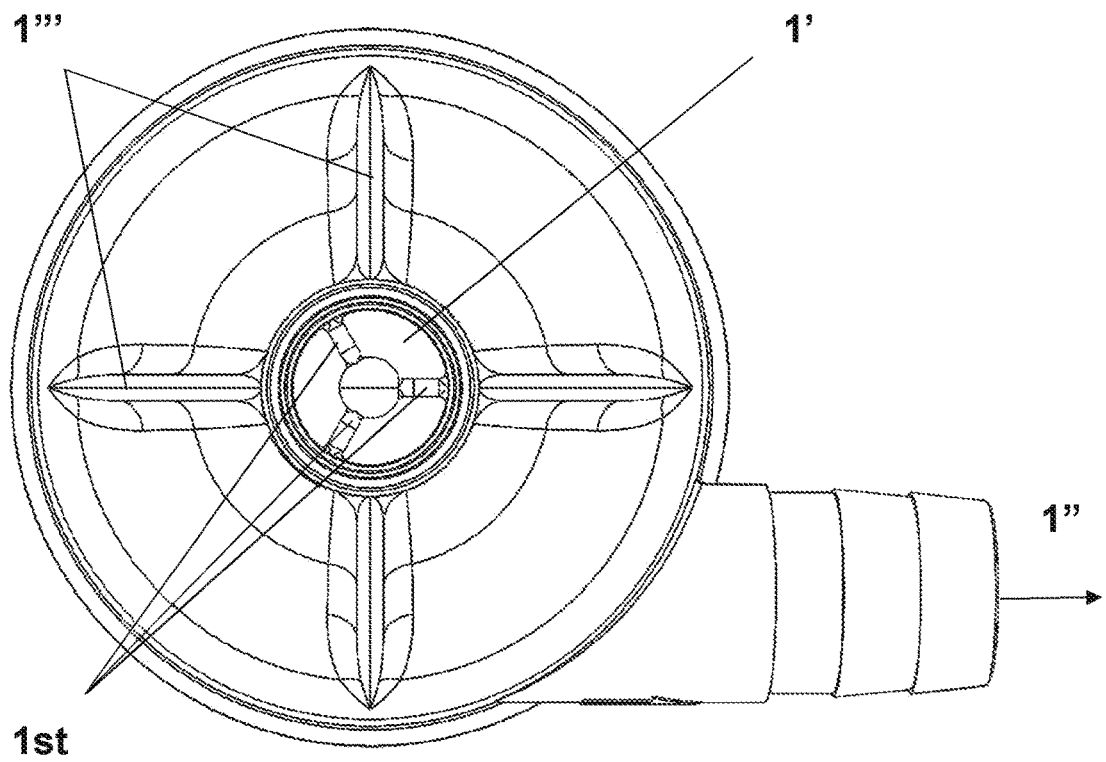
FIGS. 1a, b show a side and plan view of the pump housing.
Figure 1:
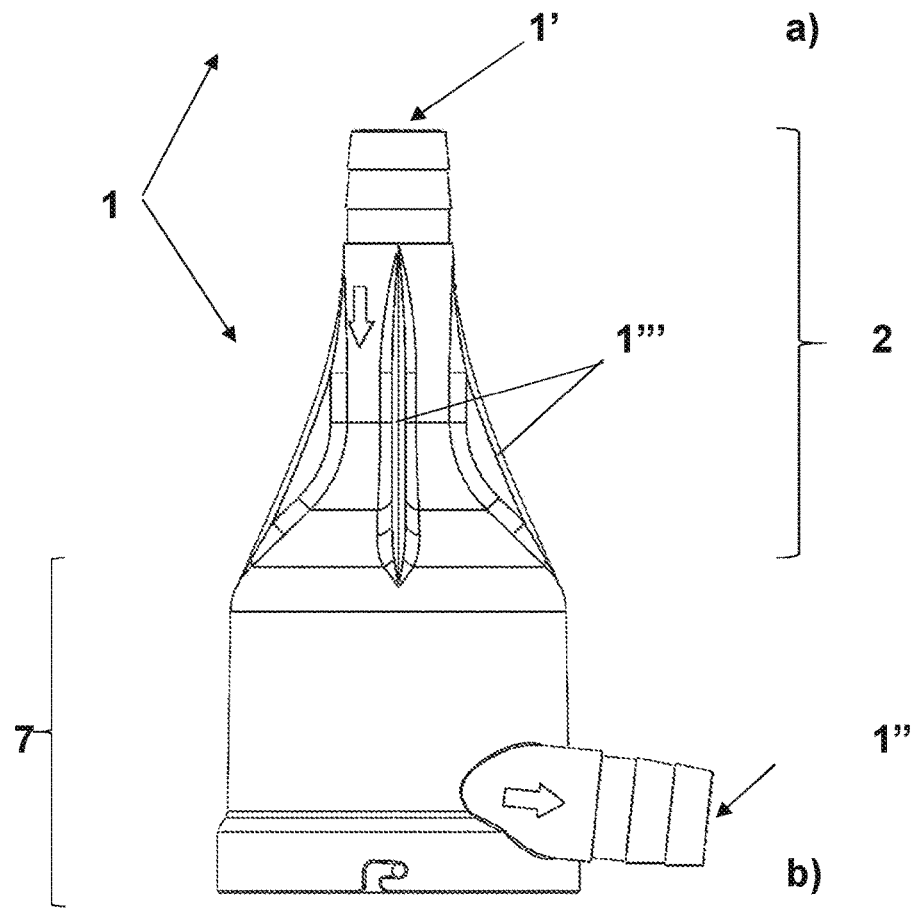

FIGS. 1a and b show a side and plan view of the pump housing 1 of the blood pump. The pump housing 1, which is substantially bottleneck-shaped in the upper portion, has a flow inlet 1' through which blood enters the blood pump through the longitudinal extent of the pump housing 1. The pump housing 1 can be divided into a bottleneck-shaped flow inlet region 2 and a hollow-cylindrical pump housing portion 7 flushly adjoining the flow inlet region. A flow outlet 1" is oriented substantially orthogonally to the flow inlet in the region of the hollow-cylindrical pump housing portion 7.

In order to keep the wall thickness of the pump housing 1 of the blood pump as thin as possible for reasons of cost and weight, among other things, four stability struts 1''' are attached to the outside of the pump housing 1 in the region of the bottleneck-shaped flow inlet region 2.

Immediately downstream from the flow inlet 1', four support struts 1st are connected on one side to the inner wall of the pump housing 1 and converge orthogonally to form an inlet star and together form the spatial attachment for the upper rotary shaft bearing, which will be discussed below. The support struts 1st are optimized in terms of flow dynamics in order to form the lowest possible flow resistance for a blood flow entering through the flow inlet 1'.

The blood pump represents a diagonal pump, in which the blood flow entering through the flow inlet 1' in the longitudinal extent of the pump housing 1 diverts orthogonally to the inflow direction into a blood flow exiting tangentially from the pump housing 1 through the flow outlet 1''.

Figure 2:
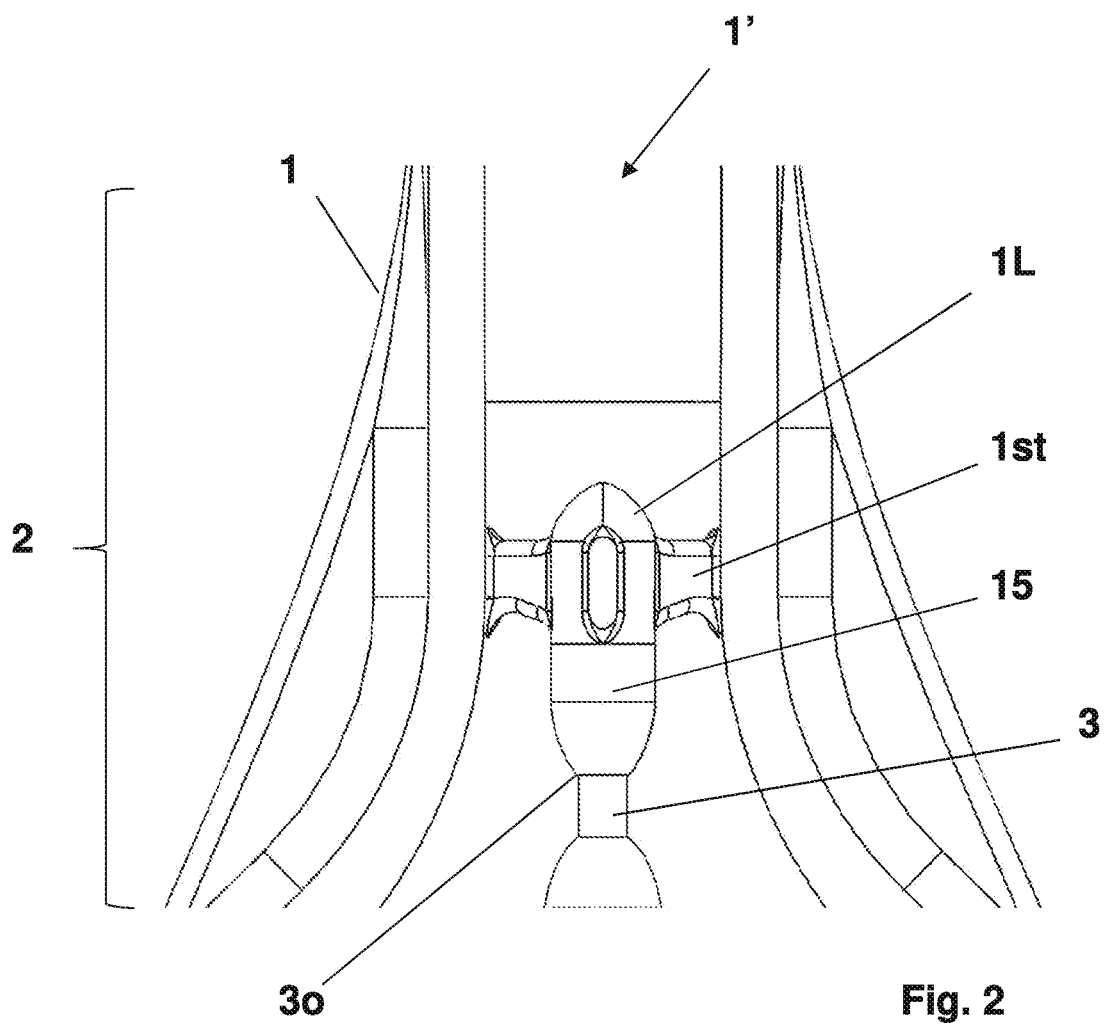
FIG. 2 shows a longitudinal sectional view through the pump housing in the region of the flow inlet.
Figure 3:
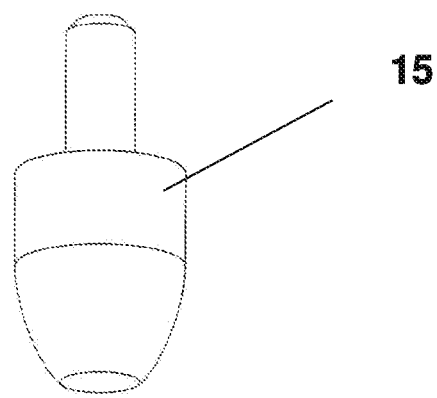
FIG. 3 shows an upper bearing element.

FIG. 2 shows a partial longitudinal portion through the upper part of the pump housing 1 in the region of the bottleneck-shaped flow inlet region 2. Downstream of the flow inlet 1' there are located the support struts 1st, which are connected in one piece to the pump housing 1, are optimized in terms of flow dynamics, converge to form an inlet star and lead centrally into a bearing structure 1L of a "capsule-like design", which is favorable in terms of flow dynamics. Preferably, the pump housing 1, together with the support struts 1st and the bearing structure 1L are formed in one piece from plastic, preferably in an injection moulding process. A bearing sleeve 15, which is preferably made of ceramic or largely wear-free plastics material, is inserted to be flush, that is without edges, within the bearing structure 1L. The upper end of the rotary shaft 3 is axially fixed and rotatably joined in the bearing sleeve. See also FIG. 3.

Figure 4:
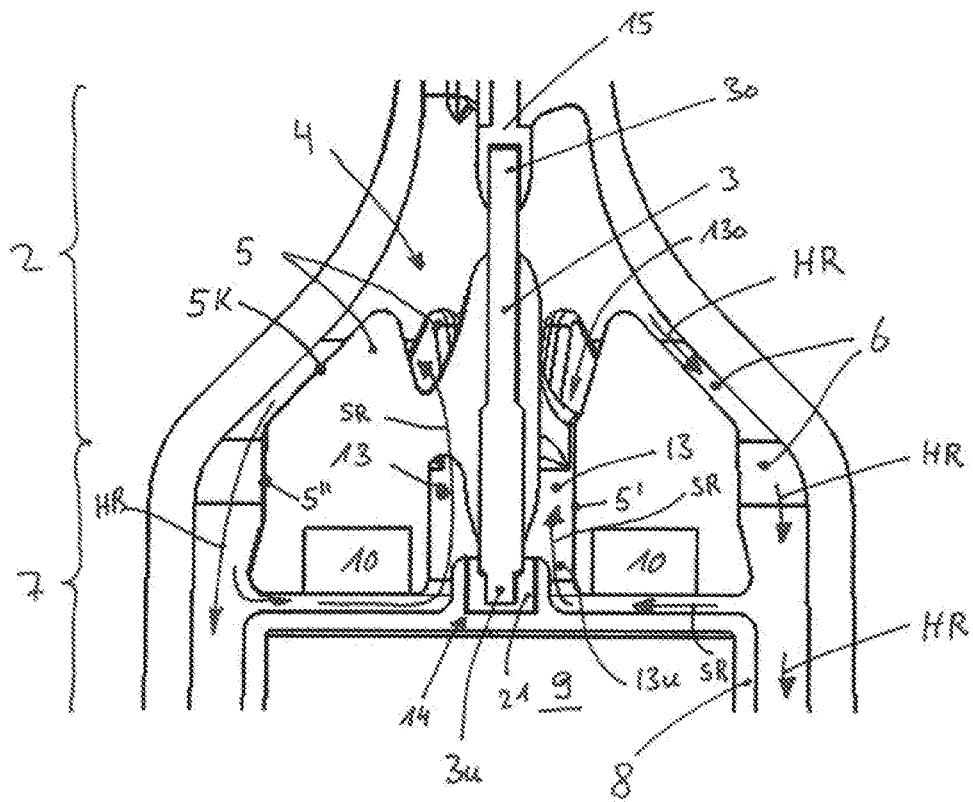
FIG. 4 shows a longitudinal sectional view through the pump housing.

FIG. 4 shows a further partial longitudinal section through the pump housing 1, showing the bottleneck-shaped flow inlet region 2 and a part of the adjoining hollow-cylindrical pump housing portion 7.

The pump housing 1 comprises a rotary shaft 3. The upper rotary shaft end 3o leads into the bearing sleeve 15 in an axially fixed and rotatable manner. A blade assembly 4 is connected to the rotary shaft 3 for conjoint rotation, and at an inner housing 8, on the upper side of a lower bearing 14 with an inlay element 21, in which the lower rotary shaft end 3u is mounted in an axially fixed and rotatable manner.

The blade assembly 4, which is connected to the rotary shaft 3 for conjoint rotation, has six flat blades 5, in which in the exemplary embodiment shown in FIG. 4 they are of the same shape and size. The six blades 5 are each arranged equidistantly around the rotary shaft 3. Their radially outer blade contours enclose a main flow channel 6 with the inner wall of the pump housing 1, with the blood flow passing through the main flow channel in the main flow direction HR during operation of the blood pump.

Figure 5:
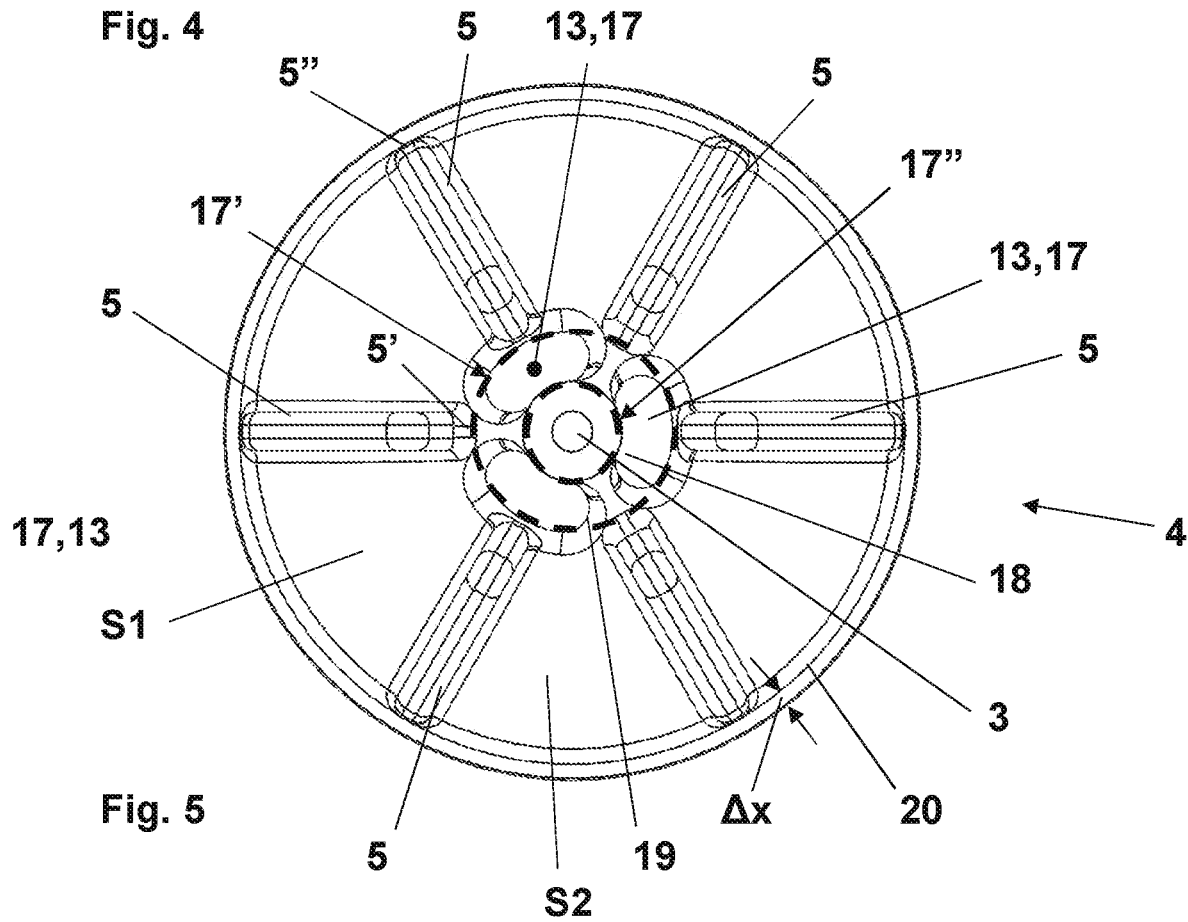
FIG. 5 shows a plan view of the blade assembly according to a first embodiment.

In addition, reference is made to FIG. 5, showing the blade assembly 4 in an axial plan view in the direction of flow. The blade assembly 4 adjoins three flushing channels 13, which are evenly distributed around the rotary shaft 3. Each of the flushing channels 13 has a kidney-shaped flushing channel cross-section 17, each of which has a convex peripheral contour 17' facing away from the rotary shaft 3 and a radially inner concave peripheral contour 17'' facing towards the rotary shaft 3.

The concave peripheral contours 17'' of the three flushing channel cross-sections 17 lie on a first virtual circular line 18 arranged centrically to the rotary shaft 3. The convex peripheral contours 17' of the three flushing channel cross-sections 17, on the other hand, lie on a second virtual circular line 19 and are arranged centrically to the rotary shaft.

In the exemplary embodiment as shown, all the blades 5 each have radial extensions with the blade ends 5' facing radially towards the rotary shaft 3 which all lie on the virtual second circular line 19 in axial projection onto the blade assembly 4. The radially outer ends 5'' of the blades 5, on the other hand, lie on a third virtual circular line 20, corresponding to the circumferential edge of the blade assembly 4 or is spaced from it by a small distance $\Delta x$, with $0.1\ mm <= \delta x <= 2\ mm$.

The three flushing channels 13 extend parallel to the axis of rotation 3 and each have a lower flushing channel opening 13u and an upper flushing channel opening 13o which are optimized in terms of flow dynamics.

Each upper flushing channel opening 13o opens into two flow regions S1, S2. Each flow region is bounded by two blades 5. The upper flushing channel openings 13o, which are each shaped like orchids, offer the lowest possible flow resistance in the case of a flushing channel flow SR oriented retrogradely to the main flow HR flowing through along the main flow channel 6, whereby the retrograde flushing flow SR is able to lead into the main flow HR in the bottleneck-shaped flow inlet region 2 largely without turbulence, but at least with a low turbulence.

The lower flushing channel opening 13u of each flushing channel 13 is also flow-optimized for the lowest possible flow resistance. For this purpose, the lower bearing 14 attached to the inner housing 8 provides flow gate oriented flow-dynamically in the direction of the lower flushing channel opening 13u and forms a lowest possible entry resistance into the various flushing channels 13 for a retrograde flushing channel flow SR.

The blade assembly 4 additionally has a magnetic coupling 10 which is magnetically coupled with a rotary motor 9 mounted inside the inner housing 8. The permanent magnets or magnetic units required for the magnetic coupling 10 are completely incorporated within the blade assembly 4, which is preferably made of a wear-free plastics material. The magnetic units can be fully encapsulated either as part of a casting process or a generative manufacturing process to create the blade assembly 4.

Figure 6:
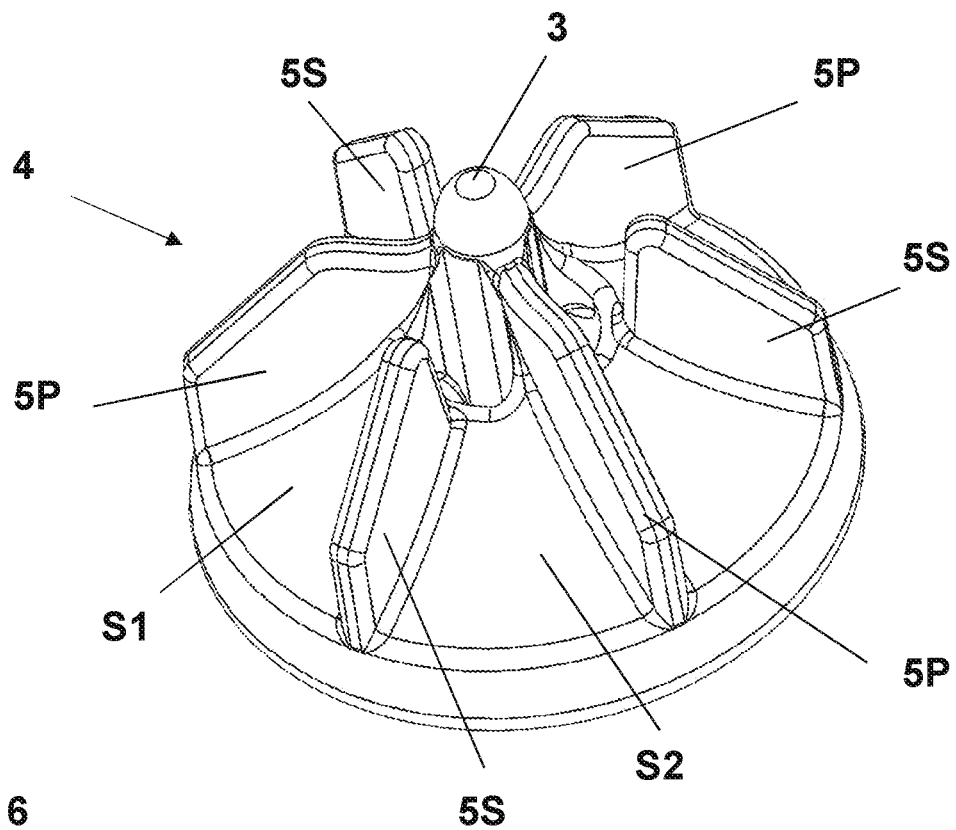
FIG. 6 shows a perspective view of the blade assembly according to a second embodiment.
Figure 7:
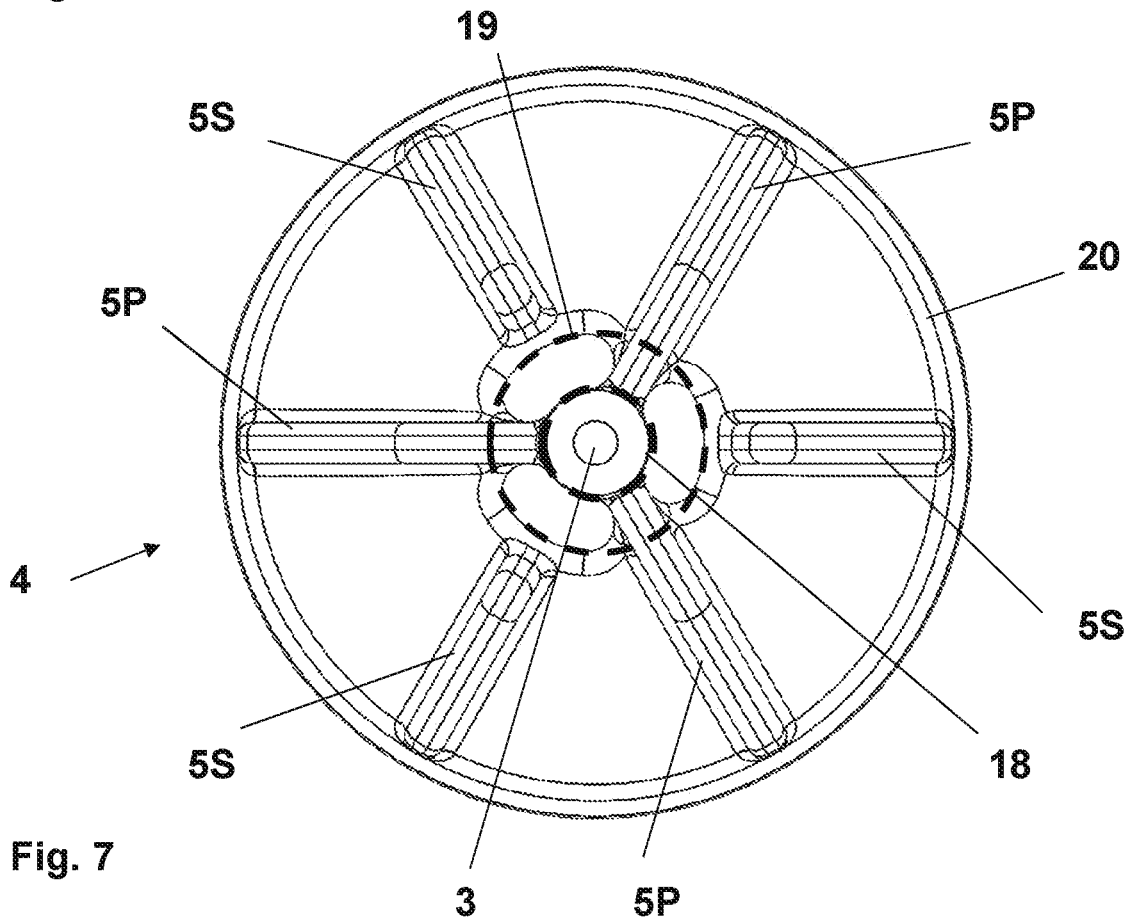
FIG. 7 shows a plan view of the blade assembly according to the second embodiment.

FIGS. 6 and 7 show an alternative embodiment for a blade assembly 4 in a perspective oblique view and an axial plan view. In contrast to the blade assembly shown in FIGS. 4 and 5, the blade assembly 4 in FIGS. 6 and 7 has three primary blades 5P of identical shape and size, which alternate in the axial arrangement around the rotary shaft 3 with secondary blades 5S of shorter radial design. All blades 5P and 5S have a flat shape. The primary blades 5P have a radial extension that extends from the first virtual circular line 18 to the third circular line 20 at the edge. The secondary blades 5S, on the other hand, only extend from the second virtual circular line 19 to the third circular line 20.

FIG. 6 shows that the upper flushing channel opening 13o opens in an orchid-like manner between two primary blades 5P, wherein in each case a secondary blade 5S divides the upper opening region into two flow regions S1 and S2.

Each of the three primary blades 5P terminate directly or indirectly at the rotary shaft 3 at their ends facing radially towards the rotary shaft 3. With the exception of their shortened radial extent, the secondary blades 5S otherwise have a planar extent of the same shape and dimensions as the primary blades 5P.

Figure 8:
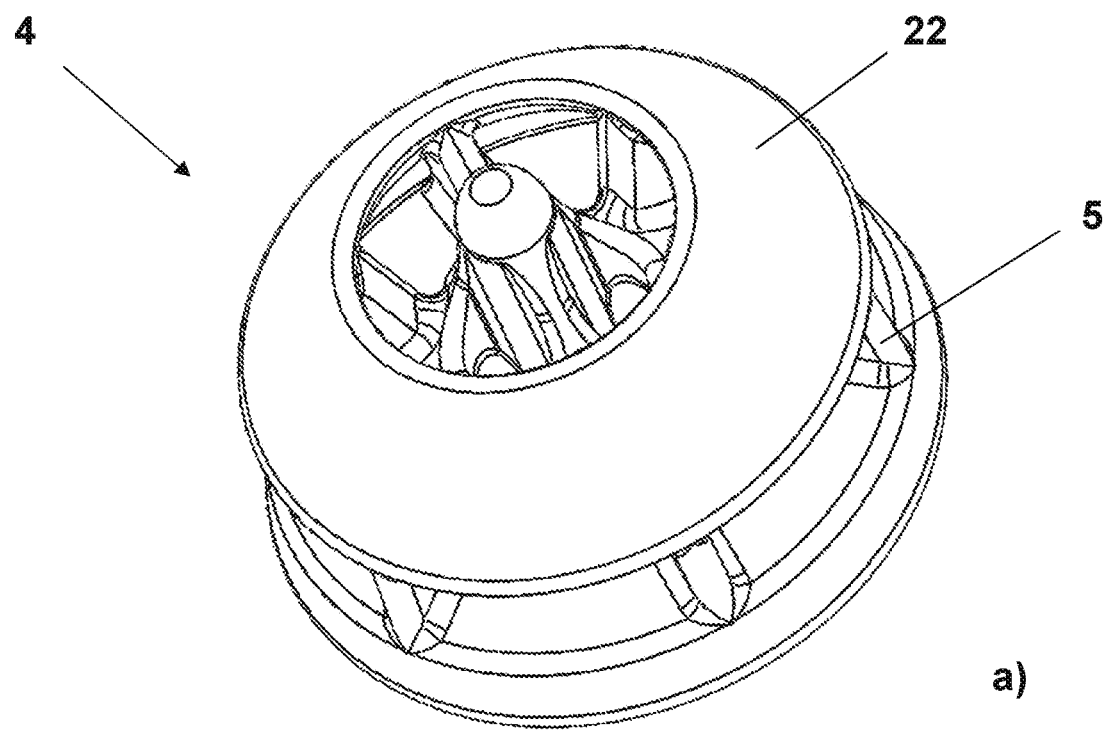
FIGS. 8a-d show multi-lateral views of a blade assembly with cover plate.
Figure 8:
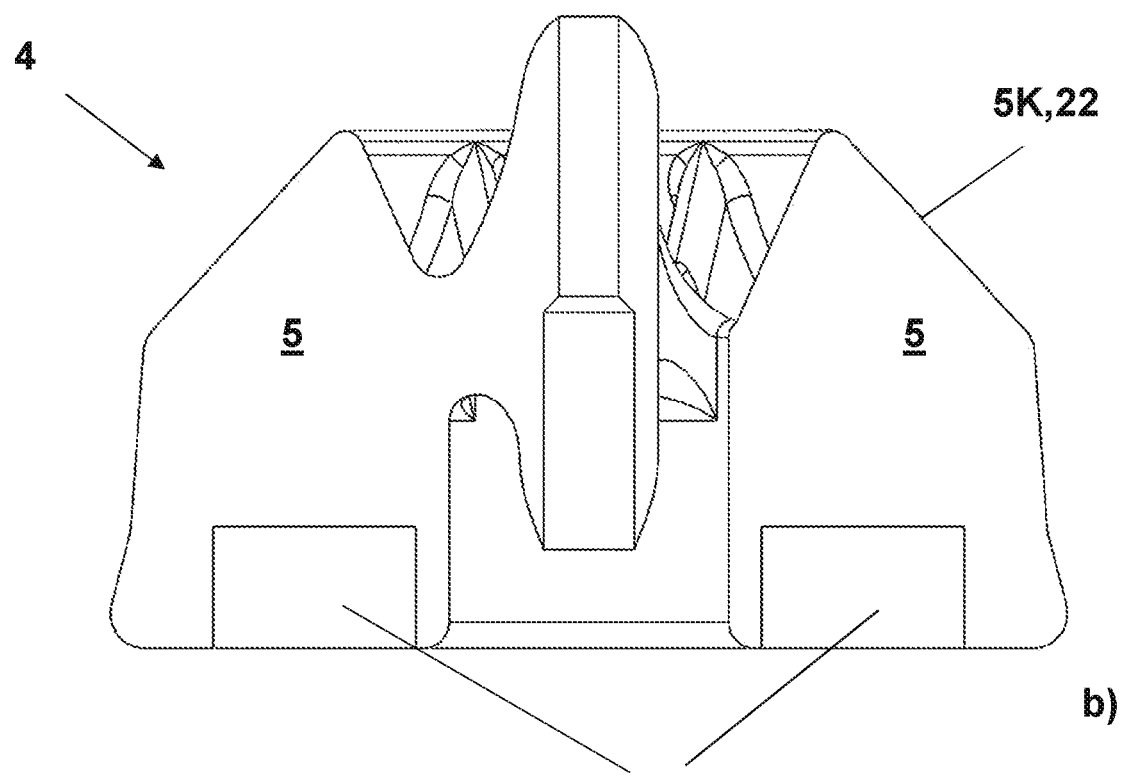
Figure 8:
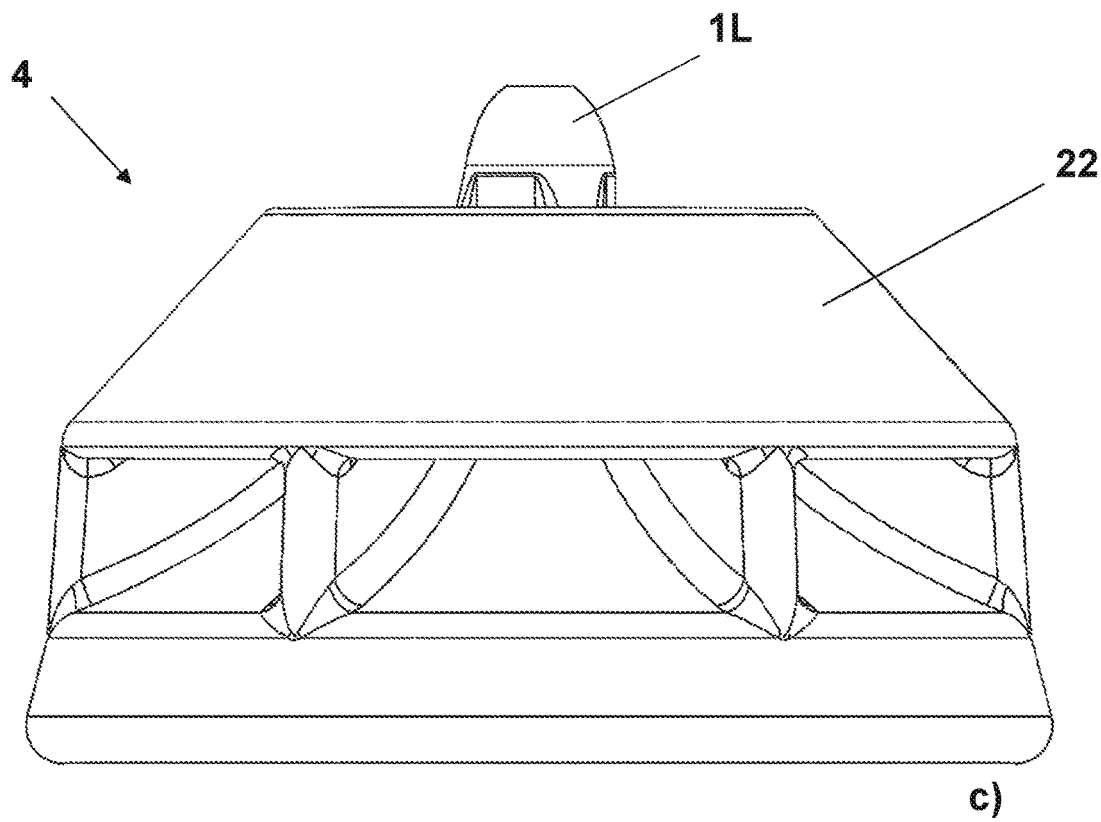
Figure 8:
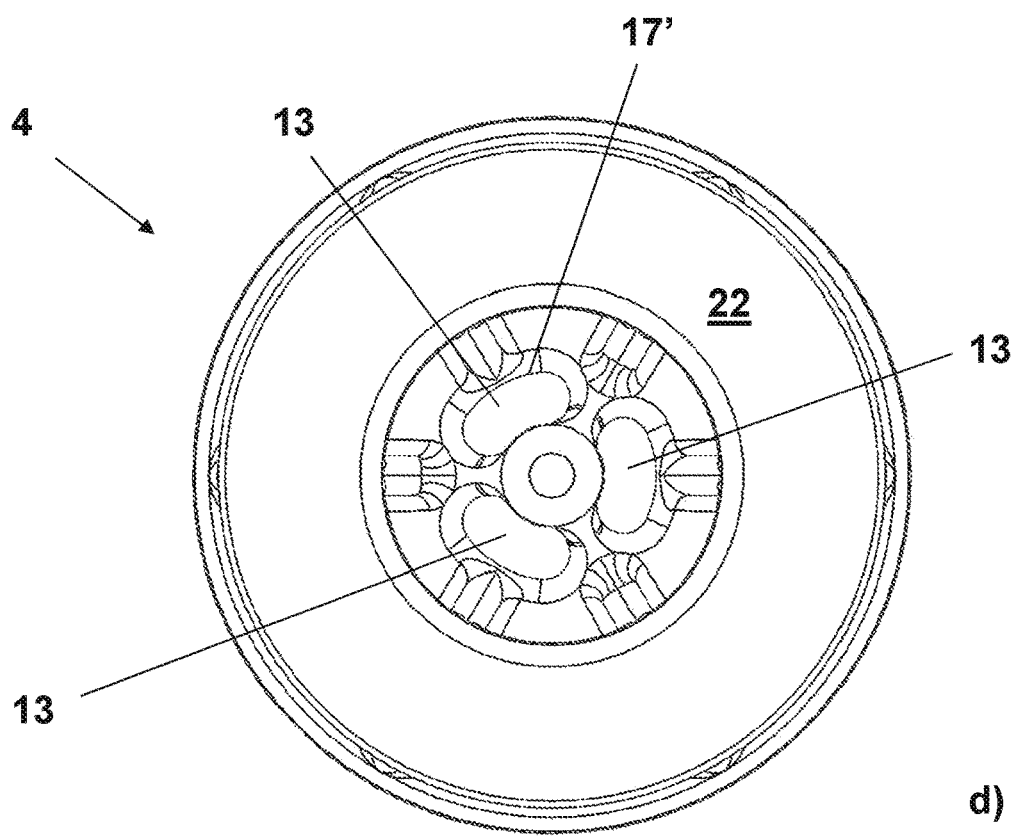

FIGS. 8a, b, c and d each illustrate an alternative embodiment of the blade assembly 4 with a cover disc 22 in various views or forms of presentation. FIG. 8a shows the blade assembly 4 in perspective view from diagonally above, FIG. 8b as longitudinal section, FIG. 8c from the side and FIG. 8d from above. The blade assembly 4 is similar to the blade assembly already shown in FIGS. 4 and 5, that is the 5 individual blades 5 are all of identical design and their radially inner blade edges 5' border on the convex peripheral contours of the 17' kidney-shaped flushing channel cross-sections 17. In addition, the side edges 5k, shown as FIG. 4, of the blades 5 face the flow and are connected to a cover disc 22 which, together with the inner wall of the pump housing 1, delimits the main flow channel 6. The cover disc 22 is conical and has an otherwise straight frustoconical surface which, together with the inner wall of the pump housing 1, delimits a main flow channel 6 which is invariably predetermined irrespective of the rotational speed of the blade assembly 4. The cover disc 22 helps to reduce the shear forces and mechanical stresses acting on the blood flow as it passes through the blood pump, allowing the blood to pass through the blood pump more gently.

Of course, it is also possible to provide the cover plate 22 on the blade assembly 4 according to the exemplary embodiments shown in FIGS. 6 and 7 accordingly.

LIST OF REFERENCE SIGNS 1 pump housing
1' flow inlet
1" flow outlet
1''' stability struts
1st support struts
1L bearing structure
2 bottleneck-shaped flow inlet region
3 rotary shaft
3o upper rotary shaft end
3u lower rotary shaft end
4 blade assembly
blades
n number of blades
5P primary blades
5S secondary blades
5' radially inner blade edge
5" radially outer blade edge
5K side edge
6 main flow channel
7 hollow-cylindrical pump housing portion
8 inner housing
9 rotary motor
magnetic coupling
11 continuing flow channel
12 secondary channel
13 flushing channel
13u lower flushing channel opening
13o upper flushing channel opening
14 lower bearing
bearing sleeve
16 flushing channel longitudinal axis
17 flushing channel cross-section
17' convex peripheral contour
17" concave peripheral contour
18 first circular line
19 second circular line
third circular line
21 inlay element
22 cover disc
SR secondary flow, flushing flow
HR main flow
S1, S2 flow regions
R1, R2, R3 radii

The invention claimed is:

1. A pump housing housing for a blood pump comprising:
a bottleneck-shaped flow inlet region, including a blade assembly mounted for rotation on a rotatable shaft, enclosing a main flow channel together with the pump housing, including a total number of n blades oriented radially to the rotary shaft, each blade being flat and disposed equidistantly around the rotary shaft, and a hollow-cylindrical portion adjoining the bottleneck-shaped flow inlet region downstream thereof in which a rotary motor is located within an inner housing, the rotary motor being rotatably connected by a magnetic coupling to the blade assembly to rotate the blade assembly, and the inner housing in conjunction with the pump housing enclosing a flow channel, which continues the main flow channel, and together with the blade assembly encloses a secondary channel, fluidically communicating with the main flow channel, the secondary channel being fluidically connected to at least one flushing channel passing through the blade assembly and opening into the bottleneck-shaped flow inlet region, the inner housing including a lower bearing facing the blade assembly for rotatably receiving a lower end of the rotary shaft, the upper end of the rotary shaft being mounted in a bearing sleeve located in the bottleneck-shaped flow inlet region which is indirectly secured to the pump housing; and
three flushing channels with each flushing channel including a longitudinal axis oriented parallel to the rotary shaft and the three flushing channels being distributed evenly around the rotary shaft and each flushing channel including a kidney-shaped cross-section in each section surrounding the rotary shaft.

2. The blood pump according to claim 1, wherein:
each cross-section is enclosed by a peripheral edge, a radially outer convex peripheral edge contour facing away from the rotary shaft and a radially inner concave peripheral edge contour facing towards the rotary shaft;
the concave peripheral edge contours are disposed on a first virtual circular line centric to the rotary shaft; and
the convex peripheral edge contours are located on a second virtual circular line centric to the rotary shaft.

3. The blood pump according to claim 1, wherein:
a total number n of blades is 6.

4. The blood pump according to claim 2, wherein:
a total number n of blades is 6.

5. The blood pump according to claim 2, wherein:
each blade has a radial extension which, in an axial projection onto the blade assembly, extends along the rotary shaft from the second virtual circular line to a third virtual circular line disposed centric to the rotary shaft; and
a radius of the second virtual circular line is smaller than a radius of the third virtual circular line.

6. The blood pump according to claim 3, wherein:
each blade has a radial extension which, in an axial projection onto the blade assembly, extends along the rotary shaft from the second virtual circular line to a third virtual circular line disposed centric to the rotary shaft; and
a radius of the second virtual circular line is smaller than a radius of the third virtual circular line.

7. The blood pump according to claim 2, comprising:
the total number of n blades is in a first group of n/2 blades which each has a radial extension in an axial projection onto the blade assembly extending along the rotary shaft from the second virtual circular line to a third virtual circular line centric to the rotary shaft with a radius of the third circular line being greater than a radius of the second circular line and is in a second group of n/2 blades which each has a radial extension in an axial projection onto the blade assembly extending along the rotary shaft from the first virtual circular line to the third virtual circular line disposed centric to the rotary shaft; and the blades of the first and second groups are each disposed in an alternating order around the rotary shaft.

8. The blood pump according to claim 3, wherein:
the total number of n blades is in a first group of n/2 blades which each has a radial extension in an axial projection onto the blade assembly extending along the rotary shaft from the second virtual circular line to a third virtual circular line centric to the rotary shaft with a radius of the third circular line being greater than a radius of the second circular line and is in a second group of n/2 blades which each has a radial extension in an axial projection onto the blade assembly extending along the rotary shaft from the first virtual circular line to the third virtual circular line disposed centric to the rotary shaft; and the blades of the first and second groups are each disposed in an alternating order around the rotary shaft.

9. The blood pump according to claim 4, wherein:
the total number of n blades is in a first group of n/2 blades which each has a radial extension in an axial projection onto the blade assembly extending along the rotary shaft from the second virtual circular line to a third virtual circular line centric to the rotary shaft with a radius of the third circular line being greater than a radius of the second circular line and is in a second group of n/2 blades which each has a radial extension in an axial projection onto the blade assembly extending along the rotary shaft from the first virtual circular line to the third virtual circular line disposed centric to the rotary shaft; and the blades of the first and second groups are each disposed in an alternating order around the rotary shaft.

10. The blood pump according to claim 1, wherein:
the lower bearing includes a pot-shaped inlay element fixed to the inner housing into which the lower end of the rotary shaft is rotatable and axially fixed and is made of a different material than a material of the inner housing.

11. The blood pump according to claim 2, wherein:
the lower bearing includes a pot-shaped inlay element fixed to the inner housing into which the lower end of the rotary shaft is rotatable and axially fixed and is made of a different material than a material of the inner housing.

12. The blood pump according to claim 3, wherein:
the lower bearing includes a pot-shaped inlay element fixed to the inner housing into which the lower end of the rotary shaft is rotatable and axially fixed and is made of a different material than a material of the inner housing.

13. The blood pump according to claim 4, wherein:
the lower bearing includes a pot-shaped inlay element fixed to the inner housing into which the lower end of the rotary shaft is rotatable and axially fixed and is made of a different material than a material of the inner housing.

14. The blood pump according to claim 5, wherein:
the lower bearing includes a pot-shaped inlay element fixedly joined to the inner housing into which the lower end of the rotary shaft is rotatable and axially fixed and is made of a different material than a material of the inner housing.

15. The blood pump according to claim 6, wherein:
the lower bearing includes a pot-shaped inlay element fixedly joined to the inner housing into which the lower end of the rotary shaft is rotatable and axially fixed and is made of a different material than a material of the inner housing.

16. The blood pump according to claim 10, wherein:
the inlay element comprises either a ceramic or of a UHM plastic.

17. The blood pump according to claim 16, wherein:
the bearing sleeve and the inlay element are made from an identical material.

18. The blood pump according to claim 1, wherein:
the blade assembly includes a cover disc delimiting the main flow channel in the pump housing.

19. The blood pump according to claim 18, wherein:
the cover disc includes a straight frustoconical surface facing towards the pump housing.

* * * * *